United States Patent [19]

Akamatsu et al.

[11] Patent Number: 5,339,816

[45] Date of Patent: Aug. 23, 1994

[54] ULTRASONIC DOPPLER BLOOD FLOW MONITORING SYSTEM

[75] Inventors: Shigeru Akamatsu, Gifu; Yuji Kondo, Mitaka, both of Japan

[73] Assignees: Aloka Co., Ltd.; Shigeru Akamatsu, Japan

[21] Appl. No.: 964,549

[22] Filed: Oct. 21, 1992

[30] Foreign Application Priority Data

Oct. 23, 1991 [JP] Japan .................. 3-275132
Nov. 18, 1991 [JP] Japan .................. 3-301963

[51] Int. Cl.$^5$ .................................................. A61B 8/12
[52] U.S. Cl. ........................ 128/661.09; 128/662.06
[58] Field of Search ................. 128/661.08, 661.09, 128/661.10, 662.01, 662.06, 692, 713, 673, 736

[56] References Cited

U.S. PATENT DOCUMENTS

| | | | |
|---|---|---|---|
| 4,237,729 | 12/1980 | McLeod et al. | 73/861.25 |
| 4,259,870 | 4/1981 | McLeod et al. | 73/861.25 |
| 4,722,347 | 2/1988 | Abrams et al. | 128/662.06 |
| 4,733,669 | 3/1988 | Segal | 128/772 |
| 4,856,529 | 8/1989 | Segal | 128/661.08 |
| 4,869,263 | 9/1989 | Segal et al. | 128/692 |
| 4,947,852 | 8/1990 | Nassi et al. | 128/662.06 |
| 4,967,753 | 11/1990 | Haase et al. | 128/662.06 |
| 5,059,851 | 10/1991 | Corl et al. | 310/334 |
| 5,078,148 | 1/1992 | Nassi et al. | 128/661.09 |
| 5,105,818 | 4/1992 | Christian et al. | 128/662.06 |
| 5,121,749 | 6/1992 | Nassi et al. | 128/692 |
| 5,125,137 | 6/1992 | Corl et al. | 29/25.35 |

FOREIGN PATENT DOCUMENTS 89310117.0  4/1990  European Pat. Off. ........ 128/661.09

OTHER PUBLICATIONS

*Cardiometrics–Continuous Accurate Monitoring of Cardiac Output*, Cardiometrics, Inc., Mountain View, Calif., 1989.

*Primary Examiner*—William E. Kamm
*Assistant Examiner*—George Manuel
*Attorney, Agent, or Firm*—Marger, Johnson, McCollom & Stolowitz

[57] ABSTRACT

A ultrasonic Doppler blood flow monitoring system is disclosed. The ultrasonic Doppler blood flow monitoring system comprises: a catheter to be inserted into a blood vessel; at least two ultrasonic transducers provided on the catheter and arranged for transmitting ultrasonic waves toward blood flow at two different angles of incidence with respect to blood flow direction and then receiving the reflected ultrasonic waves, to obtain two ultrasonic Doppler shift frequency signals due to blood flow; and a calculating section for calculating the velocity of flowing blood on the basis of the received Doppler shift frequency signals. Therefore, even if the catheter is not placed in parallel to the blood flow direction at a bent portion of a blood vessel, it is possible to continuously calculate the velocity of flowing blood accurately. In addition, it is also possible to continuously measure the amount of flowing blood equivalent to that obtained in accordance with the thermodilution measurement method by calibrating the blood flow information calculated on the basis of the ultrasonic Doppler shift frequency signals with the amount of flowing blood obtained in accordance with the thermodilution measurement method. Therefore, it is possible to continuously monitor the cardiac functions both during and after the operation.

34 Claims, 9 Drawing Sheets

ULTRASONIC DOPPLER BLOOD FLOW MONITORING SYSTEM

BACKGROUND OF THE INVENTION

1. Field of the Invention

The present invention relates to an ultrasonic Doppler blood flow monitoring system, and more specifically to a blood flow monitoring system such that a catheter provided with ultrasonic transducers or vibrators is inserted into a blood vessel to transmit and receive an ultrasonic wave signal to and from the blood flowing through the blood vessel, in order to measure the velocity of flowing blood on the basis of the ultrasonic Doppler shift signals and further to calculate the amount of flowing blood.

2. Description of the Prior Art

With the advance of the medical technique, various serious diseases difficult in surgical treatment have become operable and therefore remediable recently. In the complicated operations performed for these diseases, there exists a tendency that a long operation time is required. Therefore, it is very important for the operator to monitor the cardiac functions of a patient accurately, that is, to grasp the condition of the patient at all times during a long-time operation.

At present, there is well known a method of obtaining cardiac outputs (the amount of blood fed out of a heart) in accordance with thermodilution measurement method, as the method of monitoring the cardiac function of a patient during and after operation. In this thermodilution measurement method, a catheter is inserted from the vein through the right atrium of the heart to the pulmonary artery; cool water is injected into the right atrium through the catheter; and the cardiac output can be estimated on the basis of the change in temperature in the pulmonary artery. This catheter is provided with a balloon at the distal tip thereof. Therefore, when this balloon is expanded, it is possible to smoothly carry the catheter from the right atrium to the capillary portions of the pulmonary artery on the blood flow. The above-mentioned catheter is called SWAN-GANZ catheter and is widely used. As far as no vascular contrast medium is injected, the catheter itself can be easily inserted into the blood vessel without involving any risk.

In the case of the above-mentioned thermodilution measurement method, however, since cooling water must be injected into the right atrium of the heart, the cardiac output is to be inspected at time intervals of about one hour at the most. As a result, there exists a problem in that it is impossible to monitor the cardiac output continuously for many hours. In other words, in the thermodilution measurement method, there exists a problem in that a sudden change of the condition of a patient under operation cannot be detected immediately and therefore appropriate countermeasures to be taken are delayed. The most important functions required by anesthetists, internists, and cardiac surgeons are to monitor the cardiac functions continuously for many hours. From this standpoint, the thermodilution measurement method is not the one which can satisfy their requirements.

To overcome the above-mentioned problems involved in the thermodilution measurement method, CARDIOMETORICS Corp. has developed a system called DOPCOM/FLOWCATH (Commodity name) which can monitor cardiac functions continuously. In this monitoring system, a catheter provided with ultrasonic Doppler transducers are incorporated. The catheter is inserted into a pulmonary artery, and the ultrasonic Doppler transducers provided on the catheter emit ultrasonic waves into the blood vessel and then receive echoes returned therefrom. On the basis of the received ultrasonic Doppler signals resulted from the echoes, the inner diameter of the pulmonary artery and the velocity of flowing blood are both measured, in order to calculate the amount of flowing blood, that is, the cardiac output, so that the cardiac functions can be monitored.

The prior art catheter adopted for the above-mentioned monitoring system will be described hereinbelow with reference to the attached drawings.

Figs. 1(A) and (B) show the essential portion of a catheter 80 for the monitoring system. The catheter 80 is provided with a first ultrasonic transducer (ultrasonic vibrator) 81, a second ultrasonic transducer 82, and a third ultrasonic transducer 83. The first ultrasonic transducer 81 is disposed in the catheter 80 so that an ultrasonic wave can be transmitted and received at a predetermined angle with respect to the blood flow direction(V). The second and third ultrasonic transducers 82 and 83 are disposed in the catheter 80 facing away from each other so that the ultrasonic waves can be transmitted and received in the radial direction of the catheter 80. In this prior art monitoring system, the velocity of flowing blood is obtained on the basis of only the ultrasonic Doppler signal obtained by an ultrasonic wave transmitted and received in the single direction. In more details, the velocity component ($v_\alpha$) in the transmission and reception direction of the first ultrasonic wave is calculated on the basis of an ultrasonic Doppler shift frequency obtained by the first ultrasonic transducer 81; the calculated velocity component ($v_\alpha$) is further corrected on the basis of the angle ($\alpha$) of incidence of the ultrasonic wave with respect to the blood flow direction (V) to calculate an absolute value (v) of the velocity of flowing blood. In the above-mentioned calculation, the assumption is made that the catheter 80 is disposed in parallel to the blood flow direction and therefore the angle ($\alpha$) of incidence of the ultrasonic wave is equal to the installation angle of the first ultrasonic transducer 81 relative to the catheter 80. The above-mentioned relationship can be represented as follows:

$$v = v_\alpha / \cos \alpha$$

Further, the second and third ultrasonic transducers 82 and 83 also transmit and receive ultrasonic waves to measure the two radial distances $d_1$ and $d_2$ to the wall 91 of the blood vessel. The blood vessel diameter (D) can be expressed by an addition of the distances $d_1$ and $d_2$ and a radial distance interval de between the second and third transducers 82 and 83 as follows:

$$D = d_1 + d_2 + d_0$$

On the basis of the blood vessel diameter D, the cross sectional area of the blood vessel can be calculated as $$A = \pi D^2 / 4$$

On the basis of both the cross-sectional area (A) and the velocity (v) of flowing blood, the amount of flowing blood (Q) can be calculated as follows:

$$Q = v \times A$$

As described above, in the DOPCOM/FLOWCATH system, the velocity of flowing blood is calculated on the assumption that the orientation of the catheter 80 is in parallel to the blood flow direction (V), and further the amount of flowing blood is calculated on the assumption that the sum of the measured radial distances $d_1$ and $d_2$ between each transducer and the blood vessel wall and the distance $d_0$ between the transducers are roughly equal to the blood vessel diameter (D). However, in a case where the catheter 80 is placed in a bent portion of the blood vessel, the orientation of the catheter is not always in parallel to the blood flow direction (V), as depicted in FIG. 2. In addition, in a case where the catheter 80 is placed in the blood vessel with being offset from the center of the blood vessel as depicted in FIG. 3, the second and third transducers 82 and 83 cannot necessarily measure the blood vessel diameter accurately. Further, the cross-sectional shape of the blood vessel is not always to be circular.

As described above, in the prior art monitoring system, when the orientation of the catheter 80 is not in parallel to the blood flow direction (V), the angle ($\alpha$) of incidence of the ultrasonic wave signal is not constant. As a result, the velocity (v) of the flowing blood calculated on the basis of the above values inevitably involves an error. In addition, when the catheter 80 is disposed with being offset from the center of the blood vessel, since the measured inner diameter of the blood vessel becomes a value (D1) smaller than the actual inner diameter (D) as depicted in FIG. 3, the cross-sectional area (A) calculated on the basis of the measured inner diameter of the blood vessel inevitably involves another error. Accordingly, the amount of flowing blood (Q) calculated as a product of the velocity (v) of the flowing blood and the cross-sectional area (A) of the blood vessel also inevitably includes an error.

Further, a major part of the clinical data so far obtained is dependent upon the thermodilution measurement method, and the clinical data obtained by the DOPCOM/FLOWCATH system are still few. Therefore, it is not sufficiently reliable to use the DOPCOM/FLOWCATH system for the actual operation.

In summary, the prior art method of measuring the amount of flowing blood by use of the DOPCOM/FLOWCATH system involves the following problems:

(1) Since the calculated velocity of flowing blood and the calculated cross-sectional diameter of the blood vessel are likely to include errors, respectively, the amount of flowing blood calculated on the basis of these values is not sufficiently accurate.

(2) The clinical data obtained so far by this system is few, and therefore the clinical data enough to monitor the cardiac functions during operation are not yet accumulated.

SUMMARY OF THE INVENTION

With these problems in mind therefore, it is the object of the present invention to provide an ultrasonic Doppler blood flow monitoring system, which can measure the velocity of flowing blood continuously without being susceptible to change in the angle of incidence of the ultrasonic wave with respect to the blood flow direction.

Another object of the present invention is to provide an ultrasonic Doppler blood flow monitoring system which can measure the amount of flowing blood continuously, by using the amount of flowing blood measured in accordance with the thermodilution measurement method as the reference data.

To achieve the above-mentioned object, the ultrasonic Doppler blood flow monitoring system according to the present invention comprises: a catheter to be inserted into a blood vessel; ultrasonic transducer means provided on said catheter for transmitting ultrasonic waves toward blood flow in the blood vessel and receiving the ultrasonic waves reflected therefrom, said ultrasonic transducer means adapted to be able to obtain ultrasonic Doppler shift frequency signals due to the blood flow based on the ultrasonic waves, without being susceptible to change in an angle of incidence of each ultrasonic wave transmitted by said ultrasonic transducer means to the flowing blood within the blood vessel; and calculating means for calculating a velocity of the flowing blood on the basis of the ultrasonic Doppler shift frequency signals obtained by said ultrasonic transducer means.

According to the ultrasonic Doppler blood flow monitoring system of the present invention, since the amount of flowing blood can be measured on the basis of the ultrasonic Doppler shift frequency signals without being susceptible to change in the angle of incidence of each ultrasonic wave with respect to the blood flow direction, even if the catheter is not placed in parallel to the blood flow direction at a bent portion of the blood vessel, it is possible to continuously measure the velocity of flowing blood accurately.

In the ultrasonic Doppler blood flow monitoring system, the ultrasonic transducer means are preferably at least two ultrasonic transducers arranged in such a way that two ultrasonic waves are transmitted and received at two different angles of incidence with respect to the blood flow direction. Further, the two ultrasonic transducers are preferably arranged in such a way that angles of incidence of the two ultrasonic waves transmitted and received from and by the respective ultrasonic transducer with respect to the blood flow direction are perpendicular to each other or not intersected each other.

To achieve the above-mentioned further object, the ultrasonic Doppler blood flow monitoring system according to the present invention comprises: blood flow amount measuring means for measuring an amount of flowing blood in accordance with thermodilution measurement method; ultrasonic transducer means to be inserted into a blood vessel for transmitting and receiving ultrasonic waves in the blood vessel, said ultrasonic transducer means adated to be able to obtain ultrasonic Doppler shift frequency signals due to blood flow based on the ultrasonic waves; ultrasonic Doppler information measuring means for measuring blood flow information continuously on the basis of the ultrasonic Doppler shift frequency signals obtained by said ultrasonic transducer means; and blood flow amount calculating means for calculating an amount of flowing blood on the basis of the amount of flowing blood measured in accordance with the thermodilution measurement method and the blood flow information measured on the basis of the ultrasonic Doppler shift frequency signals.

Further, the ultrasonic Doppler information measuring means comprises ultrasonic Doppler blood flow amount measuring means for measuring an amount of flowing blood continuously on the basis of the ultrasonic Doppler shift frequency signals; and the blood flow amount calculating means comprises blood flow amount correcting means for continuously calculating an amount of flowing blood equivalent to that measured in accordance with the thermodilution measurement method, by calibrating the amount of flowing blood measured on the basis of the ultrasonic Doppler shift frequency signals with that measured in accordance with the thermodilution measurement method and by comparing the calibrated reference amount of flowing blood with the amount of flowing blood continuously measured on the basis of the ultrasonic Doppler shift frequency signals.

In the ultrasonic Doppler blood flow monitoring system of the present invention as constructed above, it is possible to continuously measure the amount of flowing blood based upon the thermodilution measurement method, by calibrating the blood flow information calculated on the basis of the ultrasonic Doppler shift frequency signals with the amount of flowing blood obtained in accordance with the thermodilution measurement method. Therefore, it becomes possible to continuously monitor the cardiac functions both during and after the operation.

Further, the ultrasonic Doppler information measuring means comprises ultrasonic Doppler blood flow velocity measuring means for measuring a velocity of flowing blood continuously on the basis of the ultrasonic Doppler shift frequency signals; and said blood flow amount calculating means comprises blood flow amount correcting means for continuously calculating an amount of flowing blood equivalent to that measured in accordance with the thermodilution measurement method, by calculating a coefficient indicative of relationship between an amount of flowing blood measured in accordance with the thermodilution measurement method and a velocity of flowing blood measured on the basis of the ultrasonic Doppler shift frequency signals and by using the calculated coefficient and the velocity of flowing blood continuously measured on the basis of the ultrasonic Doppler shift frequency signals.

The other objects, constructions and advantages of the present invention will be apparent from the following description of the preferred embodiments with reference to the attached drawings.

DETAILED DESCRIPTION OF THE PREFERRED EMBODIMENTS

Preferred embodiments of the ultrasonic Doppler blood flow monitoring system according to the present invention will be described hereinbelow with reference to the attached drawings.

Figure 1A:
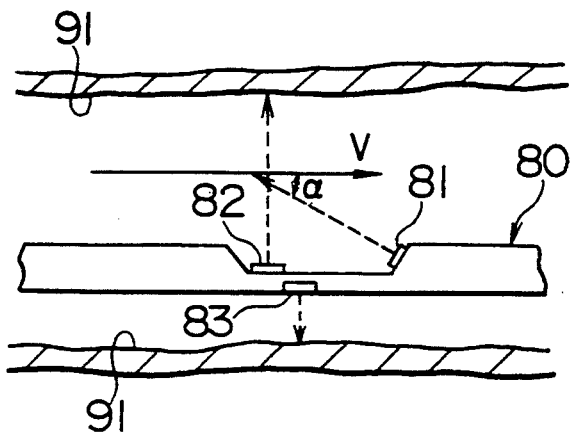
FIG. 1(A) is an illustrative side view showing a catheter of the prior art ultrasonic Doppler blood flow monitoring system, which is inserted into a blood vessel.
Figure 1B:
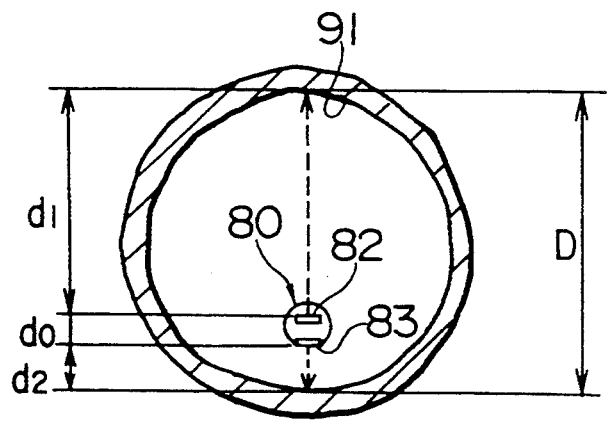
FIG. 1(B) is an illustrative cross-sectional view showing the same catheter shown in FIG. 1(A)
Figure 2:
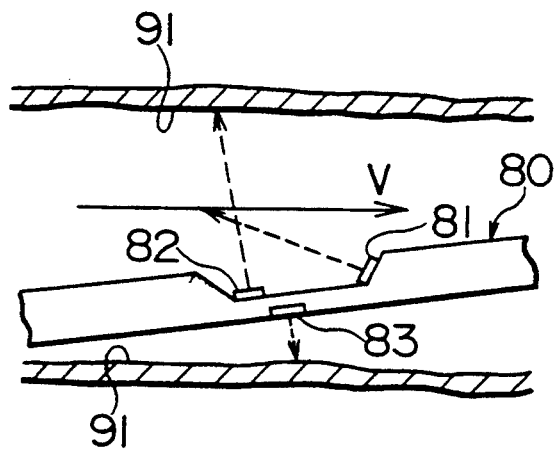
FIG. 2 is a similar illustrative side view for assistance in explaining the problem involved in the catheter of the prior art ultrasonic Doppler blood flow monitoring system.
Figure 3:
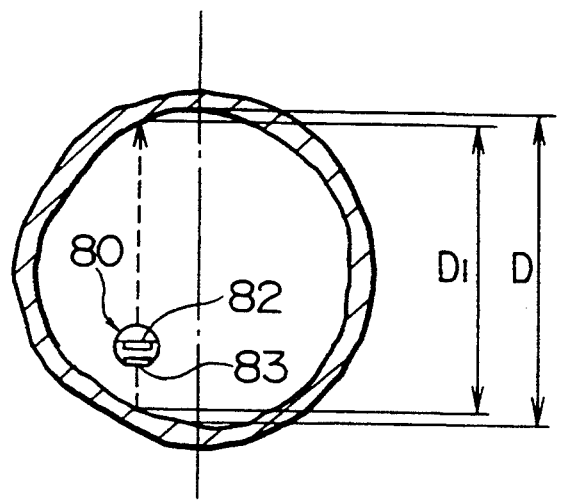
FIG. 3 is an illustrative cross-sectional view for assistance in explaining the problem involved in the catheter of the prior art ultrasonic Doppler blood flow monitoring system.
Figure 4:
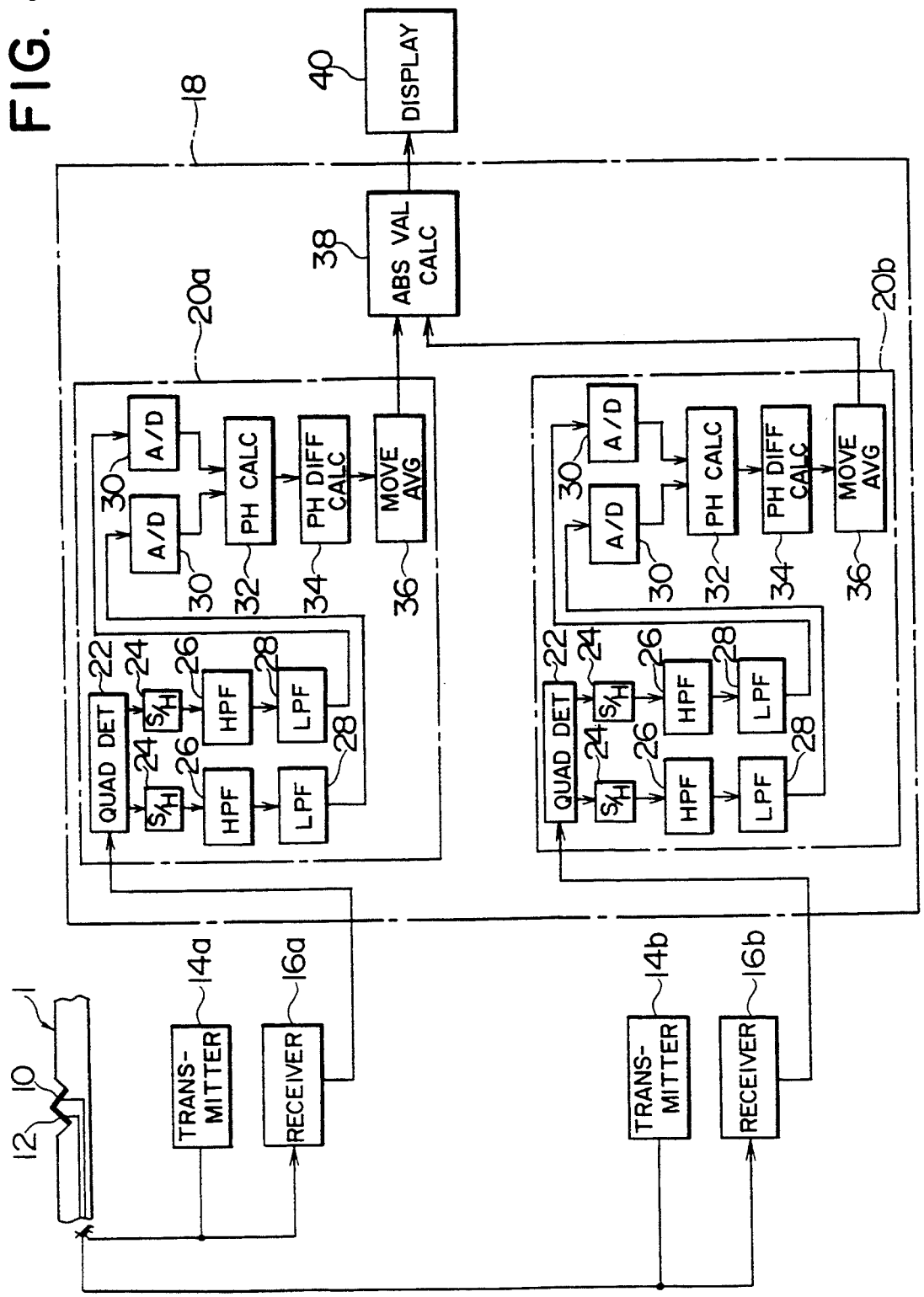
FIG. 4 is a block diagram showing an entire system configuration of a first embodiment of the ultrasonic Doppler blood flow monitoring system according to the present invention.

FIG. 4 shows an entire system configuration of a first embodiment thereof. A catheter 1 insertable into a blood vessel is provided with two ultrasonic transducers (vibrators) 10 and 12, each of which includes a single transducer element. Two transmitters 14a and 14b each for transmitting an ultrasonic transducer exciting signal are connected to the two ultrasonic transducers 10 and 12, respectively. In response to the exciting signals transmitted by the transmitters 14a and 14b, each of the ultrasonic transducers 10 and 12 transmits an ultrasonic wave into a blood vessel, respectively and further receives a reflected ultrasonic wave (echo) reflected from a blood cell in a blood of high-speed moving blood flow within the vessel, respectively. In this case, the frequency of the transmitted ultrasonic wave is different from that of the reflected ultrasonic wave due to the Doppler effect. The difference between the frequencies is called as Doppler shift. The reflected ultrasonic wave with the Doppler shift is converted into electrical signal in each transducer 10, 12. Thus generated ultrasonic Doppler shift frequency signals in the transducers 10 and 12 are fed to two receivers 16a and 16b connected to the two transducers 10 and 12, respectively, and further given to two Doppler shift frequency calculation sections 20a and 20b (included in a blood flow velocity measuring section 18) both connected to the receivers 16a and 16b, respectively. Here, both the Doppler shift frequency calculation sections 20a and 20b are the same in configuration. Therefore, only the calculation section 20a will be described hereinbelow in further details.

In the Doppler shift frequency calculation section 20a, a quadrature detector 22 detects the received signal to detect only a Doppler shift frequency signal from the reflected ultrasonic wave, and transmits the detected Doppler shift frequency signal to a sample hold circuit 24. In this processing, the detected output is divided into two channels, and processed on the basis of the two reference wave signals having a 90 degree phase difference between the both, for instance as follows: The sample hold circuit 24 extracts a Doppler shift frequency signal of any given depth from the output signal of the quadrature detector 22, and transmits the extracted signal to a high-pass filter 26 and then to a low-pass filter 28, in sequence. Here, the Doppler detection output signal includes not only a signal reflected from a high-speed moving blood flow but also an unnecessary signal (referred to as clutter) reflected from a low-speed moving substance (e.g. heart wall). Therefore, the signal extracted by the sample hold circuit 24 is passed through the high-pass and low-pass filters 26 and 28 connected in series, to remove the clutter, before being transmitted to two A/D convertors 30 arranged in parallel to each other.

The A/D convertors 30 convert the two analog signals from each of which clutter is removed, respectively into two digital signals, and transmit the respective digital signals of two channels to a phase calculator 32. The phase calculator 32 obtains a phase of the digital signal for each channel, and transmits thus obtained phase signal to a phase difference calculator 34. The phase difference calculator 34 calculates a phase difference between the two on the basis of the phases of the respective channels, and thereby calculates the velocity component in the ultrasonic wave transmit/receive direction in every pulse on the basis of the calculated phase difference. The phase difference calculator 34 transmits this obtained data to an average circuit 36. The average circuit 36 calculates an average of the velocity components based on the velocity component data which have been obtained in each pulse, and then transmits the calculated results to an absolute value calculator 38. The absolute value calculator 38 calculates an absolute value of the velocity of flowing blood based on the velocity component in each pulse on the basis of the signals obtained by the respective ultrasonic transducers 10 and 12, and outputs the calculated result to the display section 40.

Figure 5:
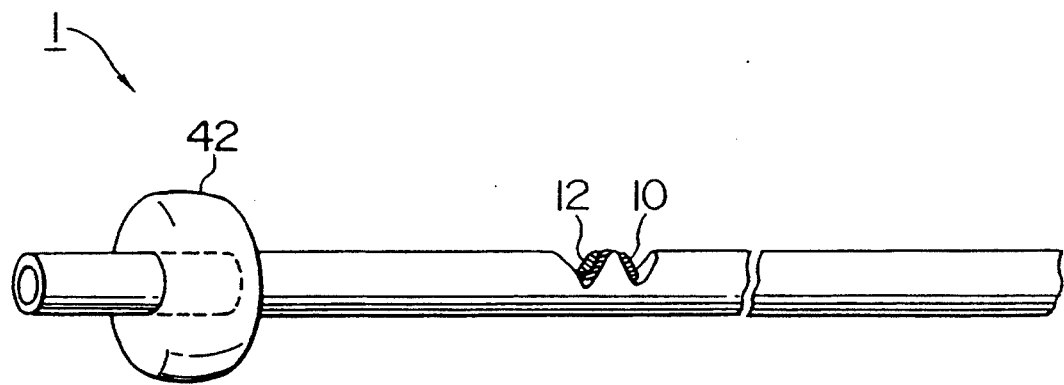
FIG. 5 is an enlarged perspective view showing a distal portion of the catheter adopted for the first embodiment of the present invention.

FIG. 5 shows in detail the distal portion of the catheter 1. As shown in the drawing, the catheter 1 is provided with two ultrasonic transducers 10 and 12 for measuring the velocity of flowing blood. The two transducers 10 and 12 are so arranged that two ultrasonic waves are emitted at two different angles of incidence with respect to the blood flow direction, respectively. In this embodiment, each ultrasonic wave has the same frequency. The frequency is preferably to be set from 5 MHz to 20 MHz. However, it is theoretically possible to constitute the transducers so as to have different frequencies with each other.

Figure 6:
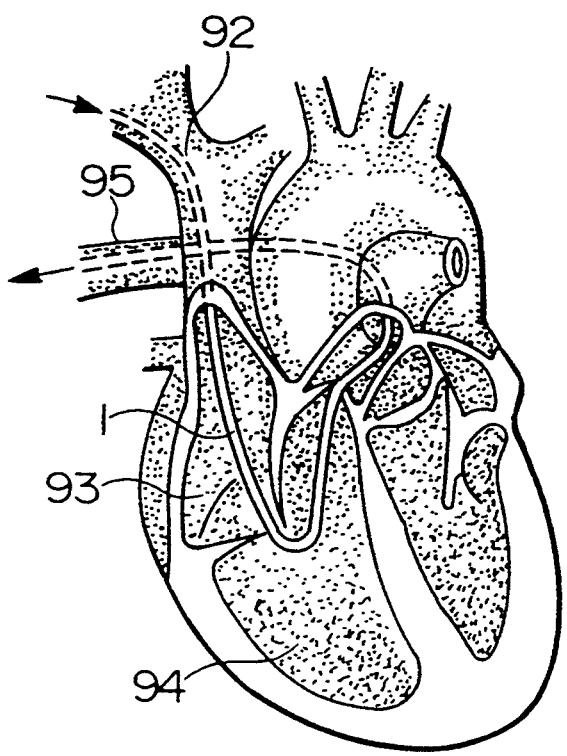
FIG. 6 is an illustration showing the state where the distal portion of the catheter reaches the pulmonary artery.

Further, the catheter 1 is provided with a balloon 42 for allowing the catheter 1 to be easily inserted into the pulmonary artery 95 through the right atrium 93 of the heart so as to be carried by the blood flow. This balloon 42 is formed of an expansible and contractible material such as rubber and is normally brought into tight contact with the catheter 1. When a working fluid such as air is injected from the outside into the balloon 42 through a lumen formed in the catheter, the balloon 42 is inflated so as to form a large diameter portion near the distal tip of the catheter 1 as shown in FIG. 5. Therefore, when the distal tip of the catheter 1 is inserted into the jugular vein or the femoral vein and then the balloon 42 is inflated, the catheter 1 is carried to the heart by the blood flow, that is, through the right atrium 93 and the right ventricle 94 up to the pulmonary artery 95. Thereafter, the balloon 42 is deflated to fix the catheter 1 in position. FIG. 6 shows the state where the catheter 1 is fixed at a predetermined position.

Under these conditions, the ultrasonic transducers 10 and 12 provided on the catheter 1 are located in the pulmonary artery 95 so as to transmit ultrasonic waves to the blood flow and further to receive the ultrasonic waves reflected from the blood flow.

Figure 7A:
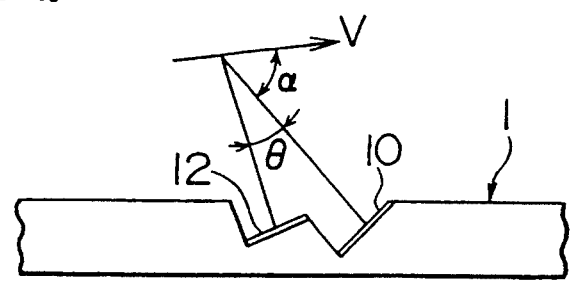
FIGS. 7(A), (B) and (C) are side views for assistance in explaining the arrangement modifications of the ultrasonic transducers of the ultrasonic Doppler blood flow monitoring system according to the present invention.

In the above-mentioned embodiment, the two ultrasonic transducers 10 and 12 are arranged on the catheter 1 in such a way that the angles ($\alpha$, $\alpha+\theta$) of incidence of the two ultrasonic waves transmitted from the respective transducers 10 and 12 with respect to the blood flow direction (V) are different from each other as depicted in FIG. 7(A). Further, the reflected ultrasonic wave signals received by these transducers 10 and 12 are converted into electrical signals, and then fed to the respective receivers 16a and 16b. The two frequencies of these two reflected ultrasonic wave signals are shifted respectively due to the Doppler shift effect in response to the velocity of flowing blood. These frequency shifts are calculated by the two Doppler shift frequency calculation sections 20a and 20b, independently. The relationship between the Doppler shift frequencies ($\Delta f_1$, $\Delta f_2$) and the absolute value of the blood flow velocity (v) can be represented as follows:

$$\Delta f_1 = (2f_c/c)v \cos \alpha \quad (1)$$

$$\Delta f_2 = (2f_c/c)v \cos (\alpha+\theta) \quad (2)$$

where
$f_c$: Frequency of transmitted ultrasonic wave
c : Sound velocity of a living body
v : Absolute value of velocity of flowing blood
$\alpha$: Angle of incidence of transmitted ultrasonic wave to the blood flow direction
$\theta$: An angle between two ultrasonic waves Therefore, by eliminating $\alpha$ by use of the two equations (1) and (2), the following equation can be obtained.

$$v = \{c/(2f_c \sin \theta)\} \times \{(\Delta f_1)^2 - 2\Delta f_1 \Delta f_2 \cos \theta + (\Delta f_2)^2\}^{\frac{1}{2}} \quad (3)$$

On the basis of the above equation (3), the absolute value calculator 38 calculates the absolute value of the velocity (v) of flowing blood without being susceptible to change in the angle of incidence of the ultrasonic waves. In this embodiment, since the ultrasonic waves are transmitted and received in the two different directions, it is possible to calculate the absolute value of the velocity (v) of flowing blood even when the catheter 1 is placed in a bent portion of the blood vessel and therefore the orientation of the catheter 1 is not in parallel to the direction of the blood flow.

As described above, in order to measure the absolute value of the velocity of flowing blood, irrespective of the angle of incidence of the ultrasonic waves with respect to the blood flow direction, at least two ultrasonic waves are the blood flow direction, at least two ultrasonic waves are transmitted and received to and from the flowing blood along two different directions. Therefore, the arrangement of the two transducers 10 and 12 in the catheter 1 as shown in FIG. 7(A) is sufficient to measure the absolute velocity of flowing blood. To facilitate the manufacturing process and the precision management of the catheter 1, however, it is preferable to arrange the two transducers 10 and 12 in intersectional positional relationship at right angles with respect to each other, as shown in FIGS. 7 (B) and (C).

In this case, since the angle $\theta$ between the two transducers is 90 degrees, the above equation (3) can be simplified as follows:

$$v = \{c/(2f_c)\} \times \{(\Delta f_1)^2 + (\Delta f_2)^2\}^{\frac{1}{2}} \qquad (4)$$

In the above-mentioned arrangement of the two transducers, it is impossible to match the respective sample points of the two transducers with each other. However, since the object of this system is to measure the velocity of flowing blood within the blood vessel, the depth of the sample point is about 1 cm at the most. Therefore, when the transducer of a 1-mm square is used, it is possible to reduce the distance between the two sample points of the respective transducers as small as 2 cm or less. If the distance between the two sample points can be reduced to such a small extent, it is possible to consider that the direction of the blood flow is roughly the same, and therefore there arises no specific problem even if the velocity of flowing blood is calculated in accordance with the above equation (4).

Figure 7B:
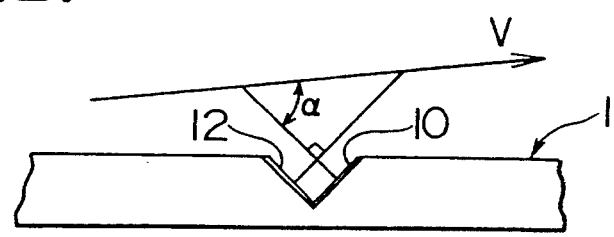
Figure 7C:
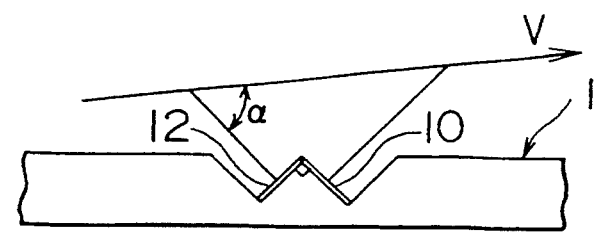

Further, in the case of the transducer arrangement as shown in FIG. 7(B), two ultrasonic waves transmitted from the two transducers intersect with each other. Therefore, it is necessary to activate the two transducers alternately so as to transmit and receive the respective ultrasonic waves in order to avoid interference between the ultrasonic waves. On the other hand, in the case of the transducer arrangement as shown in FIG. 7(C), although the distance between the two sample points is further increased, since the two ultrasonic waves transmitted from the traducers, respectively do not intersect with each other, it is possible to transmit and receive the two ultrasonic waves simultaneously, so that it is possible to measure a higher velocity of flowing blood, as compared with the case as shown in FIGS. 7(A) and (B).

As described above, in the system according to the present invention, since the absolute value of the velocity of flowing blood can be measured without being susceptible to change in the angle of incidence of the ultrasonic waves transmitted from the ultrasonic transducers with respect to the blood flow direction, it is possible to measure the velocity of flowing blood at a high accuracy, even when the catheter 1 is placed in a bent portion of a blood vessel, and thereby not arranged in parallel to the blood flow direction.

A second embodiment of the present invention will be described hereinbelow with reference to the attached drawings. In this second embodiment, the amount of flowing blood measured continuously by the ultrasonic Doppler blood flow monitoring system is compared with the amount of flowing blood measured in accordance with the thermodilution measurement method, to calculate a more accurate amount of flowing blood continuously.

Figure 8:
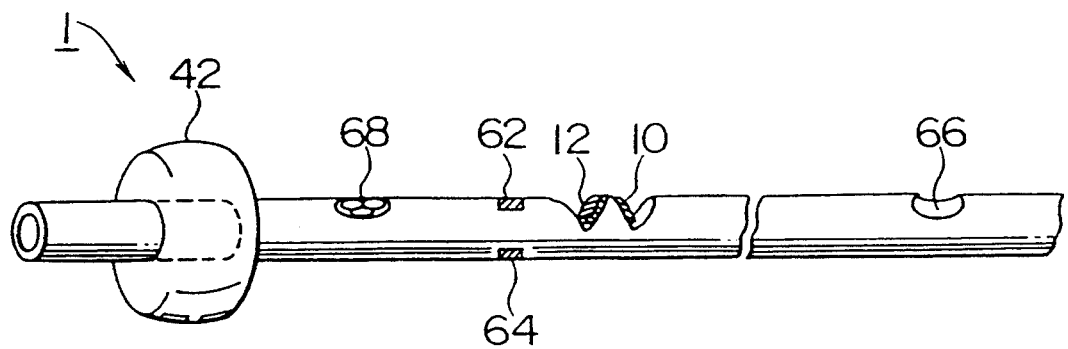
FIG. 8 is an enlarged perspective view showing a distal portion of the catheter adopted for a second embodiment of the present invention.

FIG. 8 shows the distal portion of the catheter 1 of this second embodiment. In the drawing, the catheter 1 is provided with two ultrasonic transducers 10 and 12 for measuring the velocity of flowing blood, and two other ultrasonic transducers 62 and 64 for measuring the radial distance between the inner wall (e.g. inner diameter) of the blood vessel. The two transducers 10 and 12 are arranged in the catheter 1 in such a way that the two ultrasonic waves can be transmitted therefrom, respectively at two different angles of incidence with respect to the blood flow direction. On the other hand, the two ultrasonic transducers 62 and 64 are arranged in the catheter 1 in such a way that two ultrasonic waves can be transmitted in the two opposite radial directions of the catheter 1. In addition, the catheter 1 is provided with an aperture 66 through which cool water (specific liquid) is injected into the right atrium 93 when the amount of flowing blood is measured in accordance with the thermodilution measurement method, and a temperature detector (thermistor) 68 for detecting the temperature of blood within the pulmonary artery 95. In this embodiment, it is preferable to arrange the four ultrasonic transducers 10, 12, 62 and 64 between the water injecting aperture 66 and the temperature detector 68, as shown in FIG. 8.

The balloon 42 is the same as with the case of the first embodiment, which serves to carry the catheter 1 by the blood flow through the right atrium 93 to the pulmonary artery 95 when inflated, and fix the catheter 1 in position as shown in FIG. 6 when deflated. Further, the four ultrasonic transducers 10, 12, 62 and 64 and the temperature detector 68 are arranged on the catheter 1 so as to be located in the pulmonary artery 95 when the catheter 1 is inserted, and the water injecting aperture 66 is arranged in the catheter 1 so as to be located in the right atrium 93 when the catheter 1 is inserted, in order that the amount of flowing blood can be measured under the above-mentioned arrangement conditions.

Figure 9:
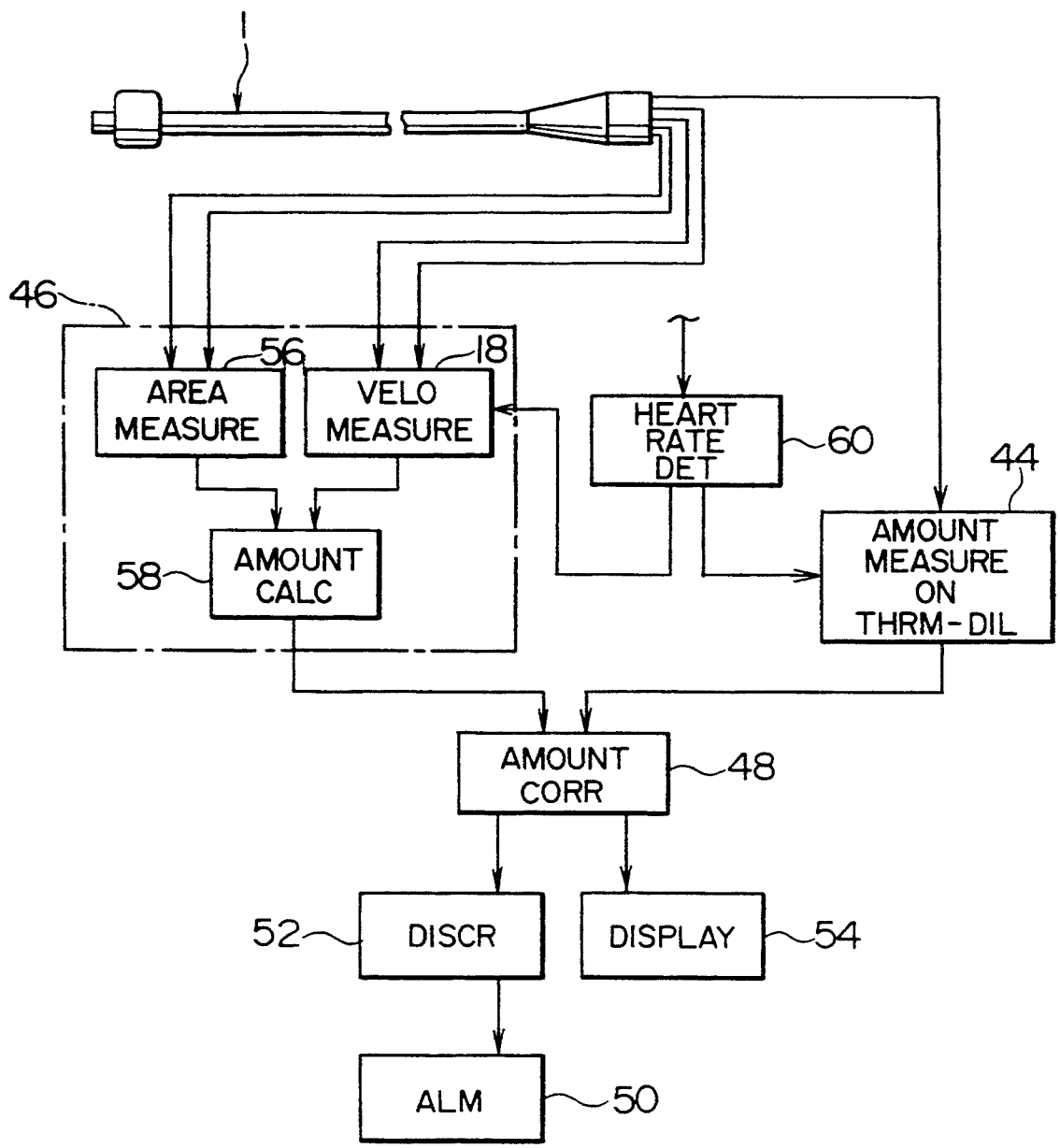
FIG. 9 is a block diagram showing an entire system configuration of the second embodiment of the ultrasonic Doppler blood flow monitoring system according to the present invention.

FIG. 9 shows an entire system configuration of the second embodiment of the present invention. The catheter 1 inserted into a blood vessel is provided with the two ultrasonic transducers 10 and 12. Ultrasonic Doppler shift frequency signals obtained by the ultrasonic transducers 10 and 12 are fed to a blood flow velocity measuring section 18 of a Doppler blood flow amount measuring section 46. A heart rate detecting section 60 detects the heart rate by electrocardiogram electrodes attached to a patient, and transmits the heart beat signal to a blood flow velocity measuring section 18 and a thermodilution blood flow amount measuring section 44. The blood flow velocity measuring section 18 is constituted into the same type as that of the first embodiment, and calculates the velocity of flowing blood in the same way as in the first embodiment. The calculated result of the velocity of flowing blood is fed to a blood flow amount calculating section 58 of the ultrasonic Doppler blood flow amount measuring section 46.

Further, the ultrasonic wave signals obtained by the ultrasonic transducers 62 and 64 are given to a blood vessel cross-sectional area measuring section 56 of the Doppler blood flow measuring section 46. On the basis of the ultrasonic wave signals obtained by the ultrasonic transducers 62 and 64, the blood vessel cross-sectional area measuring section 56 calculates the blood vessel cross-sectional area, and transmits the calculated result of the blood vessel area to the ultrasonic Doppler blood flow amount calculating section 58. On the basis of the velocity of flowing blood calculated by the blood flow velocity measuring section 18 and the blood cross-sectional area calculated by the blood vessel cross-sectional area measuring section 56, the ultrasonic Doppler blood flow calculating section 58 calculates the amount of flowing blood, and transmits the calculated result to a blood flow correcting section 48.

On the other hand, the temperature detector 68 provided on the catheter 1 detects the temperature hysteresis of the blood within the pulmonary artery 95, which is caused by injecting cool water (specified liquid) into the right atrium 93, and transmits the detected result to a thermodilution blood flow amount measuring section 44. The thermodilution blood flow amount measuring section 44 calculates the amount of flowing blood on the basis of the detected temperature hysteresis by the temperature detector 68 provided on the catheter 1 and the heart beat signal, and transmits the calculated result to the blood flow amount correcting section 48.

The blood flow amount correcting section 48 calibrates the amount of flowing blood obtained by the Doppler blood flow amount measuring section 46 with the amount of flowing blood obtained by the thermodilution blood flow amount measuring section 44, and transmits the calibrated amount of flowing blood data to a display section 54 and a discriminating section 52. The display section 54 displays the amount of flowing blood obtained by the blood flow amount correcting section 48.

On the other hand, the discriminating section 52 compares the amount of flowing blood obtained by the blood flow amount correcting section 48 with a predetermined value, and commands an alarm generating section 53 to generate an alarm when the amount of flowing blood decreases below a predetermined value. In response to the command signal generated by the discriminating section 52, the alarm generating section 53 generates an alarm to inform the operator that the amount of flowing blood drops below the predetermined value.

The method of measuring the amount of flowing blood in accordance with thermodilution measurement method will be described hereinbelow.

When a predetermined amount of cool water of a predetermined temperature is injected into the right atrium 93 through the water injecting aperture 66 provided on the catheter 1, the temperature of the blood within the right atrium drops. The blood of low temperature is fed into the right ventricle 94 and then into the pulmonary artery 95 by the beat of the heart. Therefore, where the cardiac output is large, since the blood of low temperature within the right atrium 93 is quickly fed into the pulmonary artery 95, the temperature of the blood within the pulmonary artery 95 drops quickly but also returns to the ordinary temperature quickly. On the other hand, where the cardiac output is small, it takes much time to return the temperature of the blood once dropped to the ordinary temperature. Therefore, it is possible to measure the cardiac output or the amount of flowing blood ($Q_n$) on the basis of the temperature hysteresis as described above.

Further, in the same way as with the case of the first embodiment, the amount of flowing blood is measured on the basis of the velocity (v) of flowing blood obtained by the ultrasonic Doppler shift frequency signals and the cross-sectional area of the blood vessel. To obtain the cross-sectional area of the blood vessel, two ultrasonic waves are transmitted from the two ultrasonic transducers 62 and 64 toward the blood flow flowing in the blood vessel, and the ultrasonic waves reflected from the blood flow are received, in the same way as with the case of the prior art method. The blood vessel cross-sectional area measuring section 56 calculates the radial distances to the blood vessel wall on the basis of the respective times from when the ultrasonic waves are transmitted to when the reflected ultrasonic waves are received, to calculate the cross-sectional area (A) of the blood vessel. The amount ($Q_d$) of flowing blood can be calculated on the basis of the velocity (v) of flowing blood and the blood vessel cross-sectional area (A) calculated as described above.

As described above, in the second embodiment, two amounts ($Q_n$, $Q_d$) of flowing blood can be calculated by the two methods. However, it is impossible to continuously measure the amount of flowing blood in accordance with the thermodilution measurement method, as already explained. Therefore, the amount of flowing blood is measured simultaneously in accordance with the thermodilution measurement method and the ultrasonic Doppler measurement method, and the amount ($Q_d$) of flowing blood measured by the ultrasonic Doppler method is calibrated by the amount ($Q_n$) of flowing blood measured in accordance with the thermodilution measurement method on the basis of the following equation, for instance, to obtain the corrected reference amount ($Q_{d0}$) of the flowing blood by the blood flow amount correcting section 48.

$$Q_{d0}=(Q_n+Q_d)/2 \qquad (5)$$

Once calibrated, only the amount ($Q_{d1}$) of the flowing blood by the ultrasonic Doppler method is calculated continuously to obtain the amount of flowing blood on the basis of the following equation:

$$Q=(Q_{d1}/Q_d) \cdot Q_{d0} \qquad (6)$$

Further, in this embodiment, since the ultrasonic transducers 10, 12, 62, and 64 are all arranged between the water injecting aperture 66 and the temperature detector 68, the two amounts ($Q_n$) and ($Q_d$) of flowing blood are the measurement values both obtained at almost the same positions within the pulmonary artery 95, so that the calibration accuracy is relatively high.

As described above, the cardiac output of the amount of flowing blood within the pulmonary artery 95 can be measured continuously in accordance with the method equivalent to the thermodilution measurement method. In this case, the calibration on the basis of the measurement value obtained by the thermodilution measurement method is made periodically at predetermined time intervals, where necessary.

The cardiac output or the amount of flowing blood calculated as described above is indicated on the display unit 54, so that the operator can monitor the cardiac output both during and after the operation on continuous real-time basis. In addition, in case the condition of the patient changes and therefore the cardiac output drops below a predetermined value, the discriminating section 52 commands the alarm generating section 50 to generate an alarm, so that the condition of the patient is immediately indicated to the operator.

A third embodiment of the present invention will be described hereinbelow with reference to the attached drawings.

Figure 10:
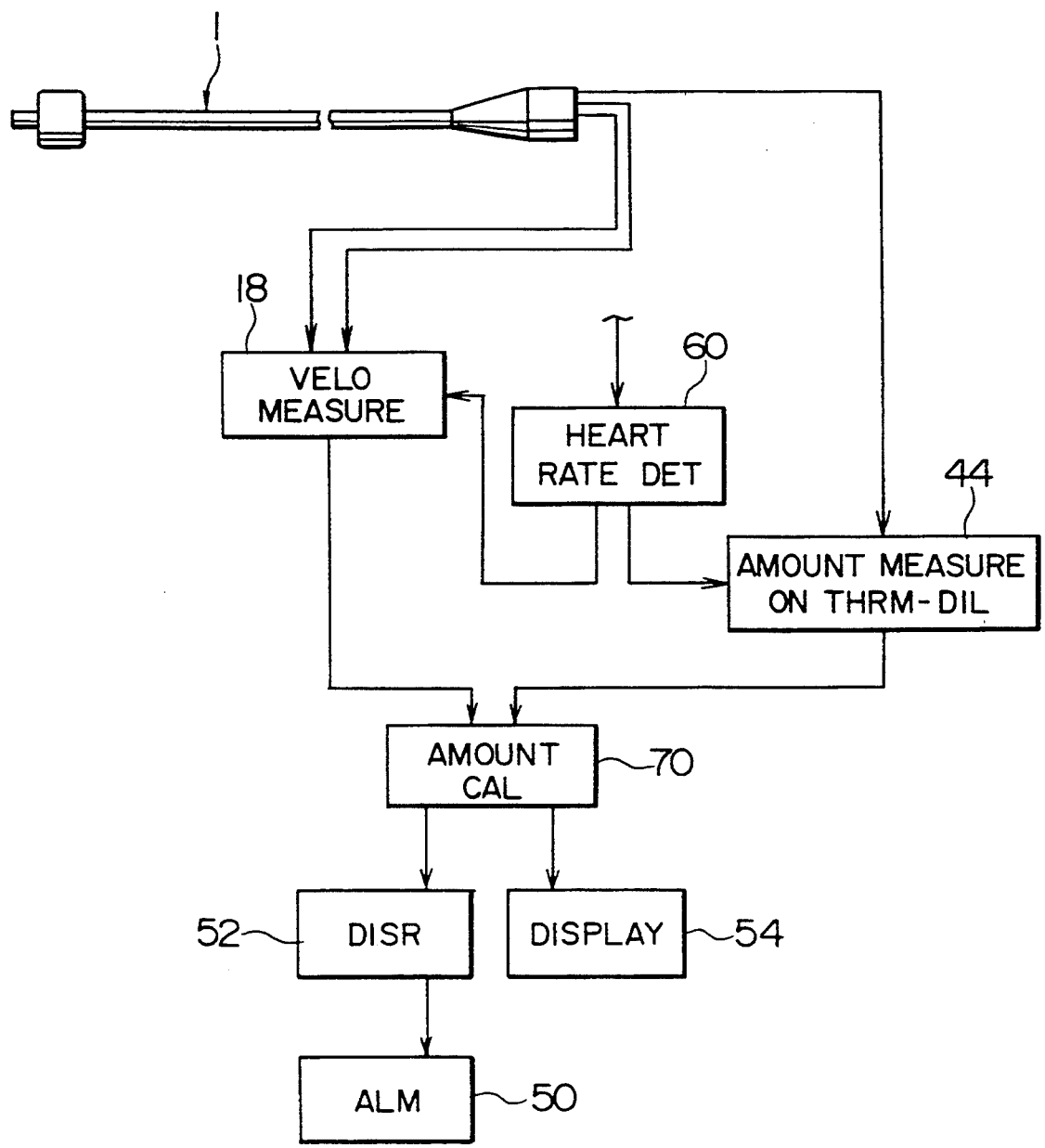
FIG. 10 is a block diagram showing an entire system configuration of a third embodiment of the ultrasonic Doppler blood flow monitoring system according to the present invention.

FIG. 10 shows an entire system configuration of the third embodiment. The different points between the third embodiment and the second embodiment are that the blood vessel cross-sectional area measuring section 56 and the ultrasonic Doppler blood flow amount calculating section 58 of the second embodiment are eliminated in this third embodiment and further the blood flow amount correcting section 48 of the second embodiment is replaced with a blood flow amount calculating section 70 in this third embodiment.

Figure 11:
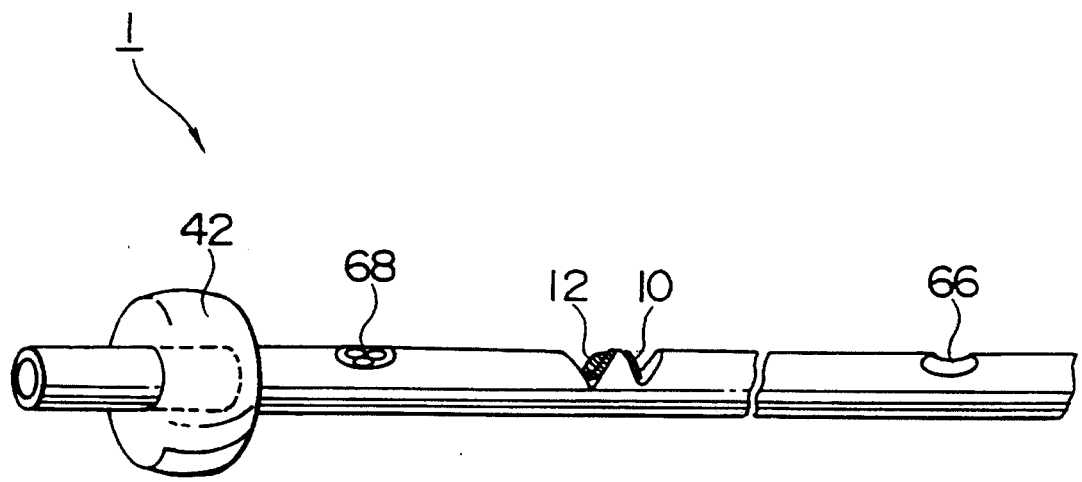
FIG. 11 is an enlarged perspective view showing a distal portion of the catheter adopted for the third embodiment of the present invention.

Further, FIG. 11 shows the distal portion of the catheter 1 of the third embodiment. The point different from the second embodiment is that no ultrasonic transducers 62 and 64 for measuring the inner diameter of the blood vessel are not provided on the catheter 1 in this third embodiment. The structural features and the functional effects of this third embodiment other than those described above are substantially the same as those of the second embodiment previously described, and therefore the same reference numerals have been retained for similar parts or sections which have the same functions, without repeating any detailed description thereof.

In the third embodiment, being different from the second embodiment, the amount of flowing blood is not directly calculated on the basis of the ultrasonic Doppler shift frequency signals, but the velocity of flowing blood obtained on the basis of the ultrasonic Doppler shift frequency signals is directly compared with the amount of flowing blood measured in accordance with the thermodilution measurement method.

The blood flow amount calculating section 70 first calculates a flow amount coefficient (k) on the basis of the amount ($Q_n$) of the flowing blood calculated by the thermodilution measurement method and the velocity (v) of flowing blood simultaneously calculated by the blood flow velocity measuring section 18 in accordance with the following equation (7), and then calculates the amount (Q) of flowing blood continuously on the basis of the velocity (v) of flowing blood and the calculated flow amount coefficient (k) in accordance with the following equation (8).

$$k = Q_n/v \quad (7)$$

$$Q = k \times v \quad (8)$$

As described above, according to the present invention, it is possible to measure the cardiac output or the amount of flowing blood continuously, and therefore to monitor the cardiac functions continuously, Consequently, it is possible to immediately detect an abrupt change of the condition of the patient and thus to enable a quick action thereagainst. In addition, there exists such an advantage that it is possible to minimize the number of thermodilution measurements by which the blood is diluted by injecting cool water into the blood vessel.

Finally, it will be apparent from the above disclosure, that many changes can be made in the specific construction and components of the system illustrated in the drawings, in accordance with the teachings of this invention, without departing from the spirit of this invention or the scope of the accompanying claims.

What is claimed is:

1. An ultrasonic Doppler blood flow monitoring system, comprising;
   blood flow amount measuring means for measuring an amount of flowing blood in accordance with a thermodilution measurement method;
   ultrasonic transducer means to be inserted into a blood vessel for transmitting ultrasonic waves toward blood flow in the blood vessel and receiving the waves reflected therefrom, said ultrasonic transducer means adapted to be able to obtain ultrasonic Doppler shift frequency signals due to blood flow based on the ultrasonic waves;
   ultrasonic Doppler information measuring means for measuring blood flow information continuously on the basis of the ultrasonic Doppler shift frequency signals obtained by said ultrasonic transducer means; and
   blood flow amount calculating means for calculating an amount of flowing blood on the basis of the amount of flowing blood measured in accordance with a thermodilution measurement method and the blood flow information measured on the basis of the ultrasonic Doppler shift frequency signals;
   wherein said ultrasonic Doppler information measuring means comprises ultrasonic Doppler blood flow amount measuring means for measuring an amount of flowing blood continuously on the basis of the ultrasonic Doppler shift frequency signals; and said blood flow amount calculating means comprises blood flow amount correcting means for continuously calculating an amount of flowing blood equivalent to that measured in accordance with the thermodilution measurement method, by calibrating the amount of flowing blood measured on the basis of the ultrasonic Doppler shift frequency signals with that measured in accordance with the thermodilution measurement method and by comparing the calibrated reference amount of flowing blood with the amount of flowing blood measured continuously on the basis of the ultrasonic Doppler shift frequency signals.

2. The ultrasonic Doppler blood flow monitoring system of claim 1, wherein said ultrasonic transducer means can obtain the ultrasonic Doppler shift frequency signals due to blood flow, based on the transmitted and reflected ultrasonic waves without being susceptible to change in an angle of incidence of the ultrasonic waves transmitted by said ultrasonic transducer means to the blood flow within the blood vessel.

3. The ultrasonic Doppler blood flow monitoring system of claim 2, wherein said ultrasonic transducer means includes at least two ultrasonic transducers arranged in such a way that the ultrasonic wave from each transducer is transmitted and received at a different angle of incidence with respect to a blood flow direction of the blood flow.

4. The ultrasonic Doppler blood flow monitoring system of claim 3, wherein said two ultrasonic transducers are arranged in such a way that an angle of intersection between the two ultrasonic waves transmitted and received by said two ultrasonic transducers is approximately 90 degrees.

5. The ultrasonic Doppler blood flow monitoring system of claim 3, wherein said two ultrasonic transducers are arranged in such a way that the two ultrasonic waves transmitted and received by said two ultrasonic transducers are not intersected with each other.

6. An ultrasonic Doppler blood flow monitoring system, comprising;
   blood flow amount measuring means for measuring an amount of flowing blood in accordance with a thermodilution measurement method;
   ultrasonic transducer means to be inserted into a blood vessel for transmitting ultrasonic waves toward blood flow in the blood vessel and receiving the waves reflected therefrom, said ultrasonic transducer means adapted to be able to obtain ultrasonic Doppler shift frequency signals due to blood flow based on the ultrasonic waves;
   ultrasonic Doppler information measuring means for measuring blood flow information continuously on the basis of the ultrasonic Doppler shift frequency signals obtained by said ultrasonic transducer means; and
   blood flow amount calculating means for calculating an amount of flowing blood on the basis of the amount of flowing blood measured in accordance with a thermodilution measurement method and the blood flow information measured on the basis of the ultrasonic Doppler shift frequency signals wherein said ultrasonic Doppler information measuring means comprises ultrasonic Doppler blood flow velocity measuring means for measuring a velocity of blood flow continuously based on the ultrasonic Doppler shift frequency signals; and said blood flow amount calculating means comprises blood flow amount correcting means for continuously calculating an amount of flowing blood equivalent to that measured in accordance with the thermodilution measurement method, by calculating a coefficient indicative of relationship between an amount of flowing blood measured in accordance with the thermodilution measurement method and a velocity of flowing blood measured on the basis of the ultrasonic Doppler shift frequency signals and by using the calculated coefficient and the velocity of flowing blood continuously measured on the basis of the ultrasonic Doppler shift frequency signals.

7. The ultrasonic Doppler blood flow monitoring system of claim 6, wherein said ultrasonic transducer means can generate the ultrasonic Doppler shift frequency signals due to blood flow based on the ultrasonic waves, without being susceptible to change in an angle of incidence of each ultrasonic wave transmitted by said ultrasonic transducer means to the blood flow within the blood vessel.

8. The ultrasonic Doppler blood flow monitoring system of claim 7, wherein said ultrasonic transducer means includes at least two ultrasonic transducers arranged in such a way that the ultrasonic wave signal of each ultrasonic transducer is transmitted and received at a different angles of incidence with respect to a blood flow direction of the blood flow.

9. The ultrasonic Doppler blood flow monitoring system of claim 8, wherein said two ultrasonic transducers are arranged in such a way that an angle of intersection between the two ultrasonic waves transmitted and received by said two ultrasonic transducers is approximately 90 degrees.

10. The ultrasonic Doppler blood flow monitoring system of claim 8, wherein said two ultrasonic transducers are arranged in such a way that the two ultrasonic waves transmitted and received by said two ultrasonic transducers are not intersected with each other.

11. An ultrasonic Doppler blood flow monitoring system, comprising:
a catheter to be inserted into a blood vessel;
at least two ultrasonic transducers provided on said catheter for transmitting ultrasonic waves toward blood flow flowing in the blood vessel in a certain direction and receiving the ultrasonic waves reflected therefrom, wherein said at least two ultrasonic transducers are arranged on the catheter such that angles determined by the blood flowing direction and each of ultrasonic wave transmitting directions of the ultrasonic transducers are different from each other and such that an angle determined by the ultrasonic wave transmitting directions of said ultrasonic transducers is set to a predetermined angle, thereby enabling the transducers to receive the reflected ultrasonic wave which have been Doppler-shifted due to the blood flow; and
calculating means for calculating a velocity of the flowing blood on the basis of the Doppler-shifted ultrasonic waves received by said ultrasonic transducers and the predetermined angle, the velocity of the flowing blood calculated independently from the angles determined by each of the ultrasonic wave transmitting directions and the blood flowing direction.

12. The ultrasonic Doppler blood flow monitoring system of claim 11, wherein said two ultrasonic transducers are arranged in such a way that the angle determined by the ultrasonic waves transmitted by each said ultrasonic transducer is approximately 90 degrees.

13. The ultrasonic Doppler blood flow monitoring system of claim 11, wherein said two ultrasonic transducers are arranged in such a way that the ultrasonic waves transmitted by each said ultrasonic transducer are not intersected with each other.

14. An ultrasonic Doppler blood flow monitoring system, comprising:
blood flow amount measuring means for measuring an amount of flowing blood in accordance with a thermodilution measurement method;
ultrasonic transducer means to be inserted into a blood vessel for transmitting ultrasonic waves toward blood flow flowing in the blood vessel and receiving the waves reflected therefrom, said ultrasonic transducer means adapted to be able to obtain the ultrasonic waves which have been Doppler-shifted due to blood flow;
ultrasonic Doppler information measuring means for measuring blood flow information continuously on the basis of ultrasonic Doppler shift frequency signals obtained by said ultrasonic transducer means based on the Doppler-shifted ultrasonic waves; and
blood flow amount calculating means for calculating an amount of flowing blood on the basis of both the amount of flowing blood measured in accordance with the thermodilution measurement method and the blood flow information measured on the basis of the ultrasonic Doppler shift frequency signals.

15. The ultrasonic Doppler blood flow monitoring system of claim 14, wherein said ultrasonic Doppler information measuring means comprises ultrasonic Doppler blood flow amount measuring means for measuring an amount of flowing blood continuously on the basis of the ultrasonic Doppler shift frequency signals; and said blood flow amount calculating means comprises blood flow amount correcting means for continuously calculating an amount of flowing blood equivalent to that measured in accordance with the thermodilution measurement method, by calibrating the amount of the flowing blood measured on the basis of the ultrasonic Doppler shift frequency signals with that measured in accordance with the thermodilution measurement method, and then by comparing the calibrated reference amount of the flowing blood with the amount of the flowing blood measured continuously on the basis of the ultrasonic Doppler shift frequency signals.

16. The ultrasonic Doppler blood flow monitoring system of claim 15, wherein said ultrasonic transducer means is arranged so as to be able to obtain the ultrasonic Doppler shift frequency signals without being susceptible to changes in an angle determined by each of the ultrasonic wave transmitting directions with respect to the blood flowing direction.

17. The ultrasonic Doppler blood flow monitoring system of claim 16, wherein said ultrasonic transducer means includes at least two ultrasonic transducers arranged in such a way that angles determined by the blood flowing direction and the ultrasonic wave transmitting direction of each ultrasonic transducer is different from each other.

18. The ultrasonic Doppler blood flow monitoring system of claim 17, wherein said two ultrasonic transducers are arranged in such a way that the angle determined by the two ultrasonic waves transmitted by said two ultrasonic transducers is approximately 90 degrees.

19. The ultrasonic Doppler blood flow monitoring system of claim 18, wherein said two ultrasonic transducers are arranged in such a way that the two ultrasonic waves transmitted by said two ultrasonic transducers are not intersected with each other.

20. The ultrasonic Doppler blood flow monitoring system of claim 16, wherein said ultrasonic transducer means includes at least two ultrasonic transducers arranged in such a way that angles determined by the blood flowing direction and the ultrasonic wave transmitting direction of each ultrasonic transducer is different from each other.

21. The ultrasonic Doppler blood flow monitoring system of claim 20, wherein said two ultrasonic transducers are arranged in such a way that the angle determined between the two ultrasonic waves transmitted by said two ultrasonic transducers is approximately 90 degrees.

22. The ultrasonic Doppler blood flow monitoring system of claim 20, wherein said two ultrasonic transducers are arranged in such a way that the two ultrasonic waves transmitted by said two ultrasonic transducers are not intersected with each other.

23. The ultrasonic Doppler blood flow monitoring system of claim 14, wherein said ultrasonic Doppler information measuring means comprises ultrasonic Doppler blood flow velocity measuring means for measuring a velocity of blood flow continuously based on the ultrasonic Doppler shift frequency signals; and said blood flow amount calculation means comprises blood flow amount correcting means for continuously calculating an amount of flowing blood equivalent to that measured in accordance with the thermodilution measurement method, by calculating a coefficient indicative of relationship between the amount of flowing blood measured in accordance with the thermodilution measurement method and a velocity of the flowing blood measured on the basis of the ultrasonic Doppler shift frequency signals, and by using the calculated coefficient and the velocity of the flowing blood continuously measured on the basis of the ultrasonic Doppler shift frequency signals.

24. The ultrasonic Doppler blood flow monitoring system of claim 23, wherein said ultrasonic transducer means is arranged so as to be able to obtain the ultrasonic Doppler shift frequency signals without being susceptible to change in an angle determined by each of the ultrasonic wave transmitting directions with respect to the blood flowing direction.

25. The ultrasonic Doppler blood flow monitoring system of claim 14, wherein said transducer means includes at least two ultrasonic transducers provided on said catheter, said at least two ultrasonic transducers being arranged on the catheter such that angles determined by the blood flowing direction and the ultrasonic wave transmitting direction of each ultrasonic transducer is different from each other and such that an angle determined by the ultrasonic wave transmitting directions of said ultrasonic transducers is set to a predetermined angle, whereby enabling to receive the reflected ultrasonic waves which have been Doppler-shifted due to the blood flow; and said ultrasonic Doppler information measuring means is adapted to measure blood flow information on the basis of the Doppler-shifted ultrasonic waves received by said ultrasonic transducers and the predetermined angle independently from the angles determined by each of the ultrasonic wave transmitting directions and the blood flowing directions.

26. The ultrasonic Doppler blood flow monitoring system of claim 25, wherein said two ultrasonic transducers are arranged in such a way that the angle determined between the two ultrasonic waves transmitted by said two ultrasonic transducers is approximately 90 degrees.

27. The ultrasonic Doppler blood flow monitoring system of claim 25, wherein said two ultrasonic transducers are arranged in such a way that the two ultrasonic waves transmitted by said two ultrasonic transducers are not intersected with each other.

28. An ultrasonic catheter, comprising:
at least two ultrasonic transducers for transmitting ultrasonic waves toward blood flow flowing in the blood vessel in a certain direction and receiving the ultrasonic waves reflected therefrom, wherein said at least two ultrasonic transducers are arranged such that angles determined by the blood flowing direction and each of ultrasonic wave transmitting directions of the ultrasonic transducers are different from each other and such that an angle determined by the ultrasonic wave transmitting directions of said ultrasonic transducers is set to a predetermined angle, whereby enabling to receive the reflected ultrasonic waves which have been Doppler-shifted due to the blood flow, and then calculate blood flow information on the basis of the Doppler-shifted ultrasonic waves received by said ultrasonic transducers and the predetermined angle independently from the angles determined by each of the ultrasonic wave transmitting directions and the blood flowing direction;
liquid injecting means for injecting a specific liquid to measure an amount of flowing blood in accordance with a thermodilution measurement method; and
temperature detecting means for detecting temperature of the flowing blood.

29. The ultrasonic catheter of claim 28, wherein said two ultrasonic transducers are arranged in such a way that the angle determined by the two ultrasonic waves transmitted by said two ultrasonic transducers is approximately 90 degrees.

30. The ultrasonic catheter of claim 29, wherein said two ultrasonic transducers are arranged in such a way that the two ultrasonic waves transmitted by said two ultrasonic transducers are not intersected with each other.

31. A method of measuring a velocity of flowing blood, comprising the steps of:
inserting a catheter having first and second ultrasonic transducers into a blood vessel;
transmitting ultrasonic waves from said first and second ultrasonic transducers toward blood flow flowing in the blood vessel in a certain direction in such a way that angles determined by the blood flowing direction and each of ultrasonic wave transmitting directions of the ultrasonic transducers are different from each other and such that an angle determined by the ultrasonic wave transmitting directions of said ultrasonic transducers is set to a predetermined angle;

receiving reflected waves which have been Doppler-shifted by the blood flow, with said first and second ultrasonic transducers;

measuring first and second ultrasonic Doppler shift frequency signals obtained on the basis of the Doppler-shifted ultrasonic waves; and calculating a velocity of the flowing blood in the blood vessel on the basis of the predetermined angle and the first and second Doppler shift frequency signals.

32. A method of measuring an amount of flowing blood, comprising the steps of:

inserting a catheter having ultrasonic transducer means for Doppler measurement into a blood vessel;

continuously measuring a velocity of the flowing blood in the blood vessel with said ultrasonic transducer means for Doppler measurement, to obtain a certain blood flow information;

injecting a liquid having a predetermined temperature into blood flowing in the blood vessel, and then measuring the amount of the flowing blood in accordance with a thermodilution measurement method based on the temperature hysteresis of the blood, during the continuous blood flow velocity measurement; and calculating an amount of the flowing blood continuously on the basis of said blood flow information and the amount of the flowing blood measured by the thermodilution measurement method.

33. The method as claimed in claim 32, wherein said step of continuously measuring blood flow velocity to obtain blood flow information includes the steps of measuring an inner diameter of the blood vessel by the ultrasonic transducer means provided on said catheter, and obtaining blood flow information representing an amount of flowing blood on the basis of the inner diameter of the blood vessel and the measured blood flow velocity; and said step of calculating the blood flow amount includes the steps of obtaining a reference amount of flowing blood by calibrating the amount of the flowing blood obtained by the ultrasonic transducer means with the amount of the flowing blood measured by the thermodilution measurement method, and calculating an amount of flowing blood equivalent to that measured in accordance with the thermodilution measurement method continuously by comparing the calibrated reference amount of the flowing blood with the amount of the flowing blood measured continuously by said ultrasonic transducer means.

34. The method as claimed in claim 32, wherein said step of calculating an amount of flowing blood includes the steps of calculating a coefficient which indicates relationship between the amount of the flowing blood measured in accordance with the thermodilution measurement method and the velocity of the flowing blood, and calculating an amount of blood equivalent to that which would be obtained in accordance with the thermodilution measurement method continuously by using the calculated coefficient and the velocity of the flowing blood continuously measured.

* * * * *